United States Patent [19]

Tocker

[11] Patent Number: 4,614,799
[45] Date of Patent: Sep. 30, 1986

[54] N-METHYLOL 4-AMINO-1,2,4-TRIAZINE-5-ONES

[75] Inventor: Stanley Tocker, Wilmington, Del.

[73] Assignee: E. I. Du Pont de Nemours and Company, Wilmington, Del.

[21] Appl. No.: 681,260

[22] Filed: Dec. 13, 1984

[51] Int. Cl.$^4$ .......................................... C07D 253/06
[52] U.S. Cl. .................................................. 544/182
[58] Field of Search ................................ 544/182, 196

[56] References Cited

U.S. PATENT DOCUMENTS 3,920,645  11/1975  Schibler et al. ...................... 544/196
4,067,724   1/1978  Draber et al. ........................ 544/182

OTHER PUBLICATIONS

Bann et al., Chemical Reviews, vol. 58, pp. 146–148, (1958).

*Primary Examiner*—John M. Ford

[57] ABSTRACT

N-methylol derivatives of herbicidal 4-amino-1,2,4-triazine-5-ones can be prepared by reacting formaldehyde with a 4-amino-1,2,4-triazine-5-one slurried in water under basic conditions. The N-methylol derivatives can be surface-modified by slurrying particles of the derivatives in water and treating with a strong acid or strong base, producing a product that releases the original herbicidal 4-amino-1,2,4-triazine-5-one in a controlled manner.

5 Claims, No Drawings

N-METHYLOL 4-AMINO-1,2,4-TRIAZINE-5-ONES

BACKGROUND OF THE INVENTION

The herbicidal properties of 3-alkylthio-4-amino-6-alkyl-1,2,4-triazine-5-ones are disclosed in U.S. Pat. No. 4,346,220. Among these compounds is metribuzin, 3-methylthio-4-amino-6-t-butyl-1,2,4-triazine-5-one. These compounds, however, even with their relatively low water solubility, are subject to leaching in the soil and run-off during rainstorms. The N-methylol derivatives of these compounds, which regenerate the parent compounds upon their own dissolution, are, however, less soluble. These derivatives provide a slow or controlled release version of the herbicidal compounds themselves. They are, therefore, useful forms of the herbicide in that they resist leaching and run-off and, among other benefits, provide greater residual activity.

The preparation of aldehyde derivatives is shown in U.S. Pat. No. 3,671,523, and the preparation in particularly of N-methylol metribuzin is disclosed in "Symposium on Controlled Release of Bioactive Materials, III", pages 7–11, A. B. Peppermen, Jr. and K. E. Savage (1979). The methods disclosed in the references involve the use of organic solvents, which are inflammable and relatively expensive. These methods are present economic disadvantages based on the need to recover and recycle the solvent in a commercial process.

SUMMARY OF THE INVENTION

The present invention provides a process for preparing an N-methylol herbicide derivative of the Formula I

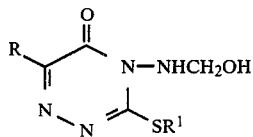

I where R is $C_3$–$C_6$ alkyl and $R^1$ is $C_1$–$C_2$ alkyl, comprising reacting formaldehyde and a compound of the Formula II

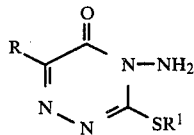

II where R and $R^1$ are as above, in water in the presence of a base providing a pH up to about 11.5.

In another aspect of the present invention, the N-methylol compound of Formula I is surface-modified by contacting it, in particulate form, in water, with an alkali metal base at a pH of about 11–13 or with a mineral acid at a pH of about 0.5–2.0. The surface modification of the N-methylol compound provides a further reduction in the release rate of the original herbicide compound of Formula II.

DETAILED DESCRIPTION OF THE INVENTION

The process of the present invention is represented by equation A, in which a compound of Formula II is reacted with formaldehyde, in a basic, aqueous medium, to provide the N-methylol derivative of Formula I:

Equation A

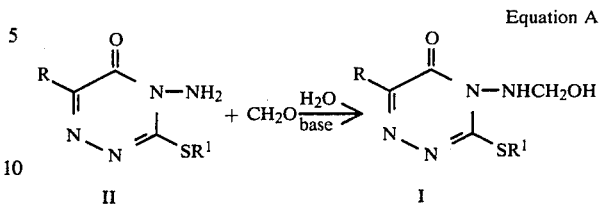

where R is $C_3$–$C_6$ alkyl and $R^1$ is $C_1$–$C_2$ alkyl. The compounds of Formula II are herbicidal and can be prepared according to the teachings of U.S. Pat. No. 4,346,220, the disclosures of which are incorporated herein by reference. The preferred starting compound is 3-methylthio-4-amino-6-t-butyl-1,2,4-triazine-5-one (R=t-butyl, $R^1$=$CH_3$; commonly known as metribuzin). The correspondingly prepared compound of Formula I is N-methylol metribuzin.

The reaction of the Formula II compounds and formaldehyde proceeds in an aqueous medium. It has been found that the Formula II compounds surprisingly need not be dissolved for the reaction with formaldehyde to proceed to completion, and therefore the need to highly dilute with water or to use organic solvents as the reaction medium is eliminated. Preferably, an aqueous suspension or slurry of the Formula II compounds is made and treated with formaldehyde. However, the reaction can proceed in unusually small amounts of water such that the reaction mixture is considerably more concentrated than is a typical suspension. That is, it has been found that the reaction can proceed so long as there is sufficient water to disperse the base effectively. It has been demonstrated that as little as 5% by weight of water or less is sufficient. As mentioned, however, it is preferred to perform the reaction in a water suspension, where up to 90 to 95% by weight of water is present.

The aqueous medium should be adjusted to a basic pH of from just above 7 to about 11.5, preferably about 8–11. Suitable bases for this purpose are alkali metal carbonates; alkali metal or alkaline earth bases, preferably hydroxides; anion exchange resins; and organic bases such as tertiary amines, pyridine, and dimethylanilines. Tertiary amines, such as triethylamine, and alkali metal bases, such as sodium hydroxide, are preferred. The aforesaid pH should be maintained throughout the reaction.

In the basic, aqueous medium, the Formula II compounds are treated with 0.5–10 moles of formaldehyde, preferably 1–10 moles of formaldehyde per mole of formula II compound. Most preferably the reactants are in equimolar amounts or at a slight molar excess of formaldehyde. Formaldehyde can be used, for example, in its commercially available form, 37% by weight aqueous solution. Alternatively, the formaldehyde can be introduced into the reaction system in a latent form, such as paraformaldehyde, which generates free formaldehyde under the desired basic conditions.

The reaction is carried out at a temperature of about 5°–90° C., preferably at about 15°–40° C. and more preferably at about 20°–25° C., and can be conducted at atmospheric pressure or in a closed system under autogenous pressure. The time of the reaction is about 1–24 hours, depending on such factors, as those skilled in the art will recognize, as temperature, reactant concentration, pH of operation, and speed of agitation. Typically, the reaction of metribuzin with an equimolar amount of formaldehyde at a pH of 9 when the reaction mixture is 50–90% by weight of water requires about four hours at a temperature of 20°–25° C.

At the completion of the reaction, the N-methylol product compound, a solid, can be recovered by simple filtration. Further washing with water, followed by drying, affords a white powder which is essentially free of unreacted starting compound.

The particles of N-methylol compound (Formula I) recovered as above are, as mentioned, a slow-release form of the free herbicide (Formula II). These particles can therefore be formulated by conventional means into a useful herbicidal composition. It is also possible to obtain useful compositions without prior isolation of the particles. That is, at the completion of the reaction of formaldehyde and Formula II compound, the resultant aqueous solution or slurry of N-methylol compound can be neutralized and formulated directly by conventional means to a stable aqueous composition.

The N-methylol compound particles, can either be formulated as is, or can be treated further. That is, the particles are susceptible to surface modification to decrease even further the rate at which the free herbicide is released. The surface-modified particles are useful as a controlled-release form of the herbicide itself.

The N-methylol compounds of Formula I, in particulate form, are suspended in water, and the suspension is then treated with either a strong acid or strong base. Optionally, the suspension or slurry of N-methylol compound particles resulting from the previously-described formaldehyde reaction sequence can be treated directly, eliminating the need for prior isolation of the particles. In either case, it has been found that the desired surface modification of the N-methylol compound particles proceeds when the pH of the slurry is adjusted to either 0.5–2.0, preferably 0.5–1.5, or to 11–13, preferably 11.5–12.5. Most preferred is to treat the slurry with a strong acid to provide a pH of about 1, or with a strong base to provide a pH of about 12. The treatment with acid or base is performed at a temperature of about 15°–90° C., preferably at about 40°–60° C., for 2 minutes to 24 hours, preferably up to 18 hours, depending on temperature. Suitable bases are alkali metal bases, such as carbonates or hydroxides of sodium or potassium. Preferred is sodium hydroxide. Suitable acids are mineral acids such as hydrochloric acid, which is preferred, sulfuric acid, or phosphoric acid. When the surface-modification is complete, the product, which is in suspended particulate form, can be filtered, washed with water, and dried.

Care must be taken to select reaction conditions from the ranges specified above which give the desired degree of surface modification of the particles but which do not lead to substantial chemical change of the compound itself. In this regard, if the reaction conditions (e.g. time, temperature, acidity or basicity) are all applied at their upper limits, excessive reaction may occur.

The particles of N-methylol compound that are the subject of this surface-modification preferably have a number-average particle size of about 1–20$\mu$, most preferably about 5–15$\mu$. It is preferred that at least about 95 percent by number of the particles be within the size range of about 2–20$\mu$, the determination of which can be made by use, for example of a Coulter Counter ®. These particle sizes can be obtained by subjecting the N-methylol compounds to standard grinding or pulverizing operations.

Although the nature of the surface modification is not known, the fact that modification of some kind does take place has been determined empirically. For example, particles of N-methylol metribuzin (number average particle size 10–15$\mu$) that have been treated with a strong acid or base as earlier described exhibit greatly reduced solubility in strong organic solvents, such as dimethylsulfoxide, compared to untreated particles. The reduction in solubility is dependent on the extent of the reaction. That is, longer reaction times or higher reaction temperatures, within the stated ranges, produce particles with more pronounced reduction in solubility. As an example of the effect of the surface modification, heat is usually required to dissolve treated particles of N-methylol metribuzin in dimethylsulfoxide to a concentration of 15–20% by weight. In contrast, untreated particles readily dissolve in this solvent to give 15–20% by weight solutions even without heating.

In further examples of the difference in characteristics, the treated particles release 50–75 percent less free metribuzin after 18 hours in excess water than do untreated N-methylol metribuzin particles. Nonetheless, elemental analysis and NMR spectroscopy show the particles to be essentially all N-methylol metribuzin, indicating that only the particle surface is modified. The nature of the product of the acid or base treatment, the surface modification, could not be determined by these analytical methods. It has been found, however, that the degree of surface modification, and consequently the extent to which the rate of release of free herbicide is decreased, is dependent on the time and severity of the treatment.

PREPARATION AND COMPARATIVE EXAMPLES

EXAMPLE 1

A mixture of 80 grams water, 10 grams technical metribuzin, and 12 grams of aqueous formaldehyde solution (37 percent weight strength, providing a large excess of formaldehyde), was treated with sufficient 10 percent aqueous sodium hydroxide, added dropwise and with agitation, to bring the mixture to a pH of 8.0. The mixture, a slurry, was stirred for 17 hours at room temperature (30°–23° C.). At the end of this time, the mixture was filtered and the remaining solids were washed with water and dried in a circulating air oven at 45° C. The resulting material, a white solid, was recrystallized from ethanol to give 8.1 grams of N-methylol metribuzin, melting point 178° C., the structure of which was confirmed by NMR spectroscopy and elemental analysis. The NMR scan showed the absence of the —NH$_2$ peak at 5.1 ppm, characteristic of metribuzin, and showed the presence of a new bond at 4.3–4.6 ppm characteristic of the —CH$_2$— group of the N-methylol derivative.

EXAMPLE 2

The procedure of Example 1 was repeated except that only 3.8 grams of the 37 percent formaldehyde solution, representing about a single equivalent of formaldehyde, was used in the mixture. At completion of the reaction and recovery procedures, as described in Example 1, weighing of the product and NMR spectroscopy confirmed that complete conversion of metribuzin to N-methylol metribuzin had occurred.

EXAMPLE 3

The procedure of Example 1 was repeated except that instead of stirring for 17 hours, at room temperature, the mixture was permitted to stand, without agitation, for 17 hours in a refrigerator at 7° C. At the end of this time, and at completion of the recovery procedures as described in Example 1, the NMR scan confirmed that complete conversion of the metribuzin to N-methylol metribuzin had occurred.

EXAMPLE 4

A mixture of 80 grams water, 10 grams technical metribuzin, and 3.8 grams of 37% aqueous formaldehyde solution was treated with sufficient 10% weight-strength aqueous sodium hydroxide solution, added dropwise with agitation, to bring the pH of the mixture to 9.5. The mixture was stirred for 2 hours at 50° C. At the end of this time, the product was recovered as described in Example 1. Weighing of the product and NMR spectroscopy indicated complete conversion to N-methylol metribuzin.

EXAMPLE 5

A mixture of 10 grams technical metribuzin, 1.4 grams paraformaldehyde, 0.5 ml of water, and 0.2 g of triethylamine was allowed to stand in a closed container for about 17 hours, without stirring, at 45°–50° C. At the end of this time, the product was recovered as described in Example 1. Weighing of the product and NMR spectroscopy indicated 90% conversion of the metribuzin to N-methylol metribuzin.

EXAMPLE 6

A mixture of 3200 grams water, 1000 grams technical metribuzin, and 400 grams of aqueous formaldehyde solution (37% weight strength) was stirred rapidly in an intensive mixer (Osterizer) and the pH of the mixture was adjusted to 9.0–9.5 with 10% weight strength aqueous NaOH. Stirring of the mixture was continued for 4 hours at room temperature (20°–23° C.). At the end of this time, the mixture was filtered, and the retained solids were dried in a circulating air oven at 45° C. The resulting solid, which was confirmed to be N-methylol metribuzin, was hammermilled from an average particle size of 25μ to an average size of 10μ.

EXAMPLE 7

A mixture of 5.0 grams of N-methylol metribuzin, prepared as in Example 6, and 50 grams of water was treated with 5% weight strength aqueous hydrochloric acid to adjust the pH to about 1.0. The mixture was stirred for about 17 hours at 20°–23° C. At the end of this time, the mixture was filtered and the solids were washed with water and dried. NMR spectroscopy and elemental analysis indicated no essential difference from untreated N-methylol metribuzin from Example 6, but the acid-treated particles were less soluble in dimethyl sulfoxide than were the untreated particles.

EXAMPLE 8

The surface-modification procedure of Example 7 was followed except that instead of stirring for 17 hours at 20°–23° C., the mixture was stirred for 30 minutes at 50° C. The acid-treated product indicated no essential difference from untreated N-methylol metribuzin, as shown by NMR spectroscopy and elemental analysis, but the product exhibited a decreased rate of solubility in dimethyl sulfoxide.

EXAMPLE 9

The surface-modification procedure of Example 7 was repeated except that phosphoric acid was used to adjust the pH and the surface reaction was conducted for only 2 hours. The treated particles indicated no essential difference from untreated N-methylol metribuzin, as shown by NMR spectroscopy, but exhibited a decreased rate of solubility in dimethyl sulfoxide.

EXAMPLE 10

A slurry of 10 grams of particles of N-methylol metribuzin, prepared as in Example 6, in 100 ml of water was treated with 10% weight strength aqueous sodium hydroxide to provide a pH of 12.0. The slurry was heated with stirring at 50° C. for 30 minutes, at the end of which time the mixture was allowed to cool, and the solids strained, washed with water, and dried. The base-treated particles exhibited no essential difference under NMR spectroscopy from untreated N-methylol metribuzin, but the product was less soluble in dimethyl sulfoxide.

EXAMPLE 11

A dispersion of 20 grams of N-methylol metribuzin in 200 ml of water was heated, with stirring, to 50° C. The pH of the suspension was adjusted to 1.0 with 5% aqueous hydrochloric acid. Stirring was continued at 50° C., and 10 ml aliquot samples of the suspension were drawn off at 5-minute, 10-minute, 20-minute, and 40-minute intervals. The solids were filtered from each sample, washed with water, and dried. Following this, 0.08 g of the particles resulting from each sample were placed in a separate vial containing 160 ml of water, sufficient water to dissolve the weight of free metribuzin available from the tested 0.08 g portion of solids. The vials were allowed to stand at 20°–23° C. and the samples were periodically analyzed by ultraviolet spectroscopy to determine the percentage of available free metribuzin that had been released from the surface-modified N-methylol form. The results, tabulated below, indicate that the release rates decrease as the time of acid treatment increases.

| Treatment Time of Sample (minutes) | % Metribuzin Released | | |
| --- | --- | --- | --- |
| | 18 hours | 4.5 days | 7 days |
| 0 (control) | 21 | 57 | 72 |
| 5 | 17 | 47 | 52 |
| 10 | 12 | 32 | 46 |
| 20 | 9 | 27 | 37 |
| 40 | 6 | 19 | 30 |

COMPARATIVE EXAMPLE

The surface-modified N-methylol metribuzin products of examples 7–10, the unmodified N-methylol metribuzin of example 6, and technical metribuzin as a control were each placed in a separate vessel, each of which contained sufficient water to dissolve the weight of free metribuzin available from the tested products. The tested products, all of which were in particulate form, remained in the water for 18 hours at 20°–23° C. At the end of that time, analysis was conducted to determine the percentage of available free metribuzin that had been released from the N-methylol form. The results are tabulated below. It can be seen that the surface modified particles of Examples 7–10 released less metribuzin than did the unmodified particle of example 6.

| Material | Free metribuzin released after 18 hours in excess water (% of available Metribuzin) |
| --- | --- |
| Technical metribuzin (control) | 100 |
| N—methylol metribuzin (Example 6) | 18 |
| Surface-modified N—methylol metribuzin | |
| Product of Example 7 | 5 |
| Product of Example 8 | 6 |
| Product of Example 9 | 11 |
| Product of Example 10 | 6 |

FORMULATIONS

The surface-modified particles of N-methylol compounds are controlled-release forms of the free 1,2,4-triazine-5-one herbicides of Formula II. The surface-modified N-methylol derivatives can therefore be formulated into useful herbicidal compositions. The formulations, which can be prepared in conventional ways, include dusts, granules, pellets, suspensions, wettable powders, and the like. Many of these can be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Percent by Weight | | |
| --- | --- | --- | --- |
| | Active Ingredient | Diluent(s) | Surfactant(s) |
| Wettable Powders | 20–90 | 0–74 | 1–10 |
| Oil Suspensions | 5–50 | 40–95 | 0–15 |
| Aqueous Suspensions | 10–50 | 40–89 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents are described in Marsden, "Solvents Guide", 2nd. Edn., Interscience, New York, 1950. Solubility under 0.1% is preferred for suspension concentrates. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Fine solid compositions are made by blending and, usually, grinding as in a hammer or fluid energy mill. Suspensions are prepared by wet milling (see, for example, Littler, U.S. Pat. No. 3,060,084). It should be noted, however, that the surface-modified N-methylol compound particles themselves should not be further ground or milled, to keep the modified surface of the particle intact. The particles of N-methylol compound can be ground or milled to the desired size before the surface-modification is conducted to avoid the need for subsequent operation on them. Granules and pellets can be made by spraying the active material upon performed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8–59ff.

The formulations of surface-modified N-methylol compounds represent a slow-release form of 1,2,4-triazine-5-use herbicides disclosed in U.S. Pat. No. 4,346,220. The specific utilities and rates of application of the formulations of the present invention will therefore be as described in that patent, the relevant disclosure of which is hereby incorporated by reference.

What is claimed is:

1. A process for preparing an N-methylol derivative of the Formula I $$\underset{N\diagdown_{N}}{\overset{R}{\underset{\parallel}{\diagup}}\overset{O}{\underset{\diagdown}{\diagup}}} \overset{}{\underset{SR^{1}}{\diagup}} N-NHCH_2OH \qquad I$$

where R is $C_3$–$C_6$ alkyl and $R^1$ is $C_1$–$C_2$ alkyl, comprising reacting formaldehyde and a compound of the Formula II $$\underset{N\diagdown_{N}}{\overset{R}{\underset{\parallel}{\diagup}}\overset{O}{\underset{\diagdown}{\diagup}}} \overset{}{\underset{SR^{1}}{\diagup}} N-NH_2 \qquad II$$

where R and $R^1$ are as above, in a water-based suspension in the presence of a base the pH being just above 7 to about 11.5, the reaction temperature about 5° to 90° C. and the base being selected from alkali metal carbonate, alkali metal hydroxide, alkaline earth metal hydroxide, tertiary amine, pyridine, dimethylaniline and anion exchange resin.

2. The process of claim 1 wherein the particles of Formula I compound have a number average particle size of 1–20μ and 95% by number of the particles are from 2–20μ in size.

3. The process of claim 2 wherein the mixture is treated with a carbonate or hydroxide of an alkali metal.

4. The process of claim 2 wherein the mixture is treated with hydrochloric acid or phosphoric acid.

5. The process of claim 2 wherein the Formula I compound is N-methylol metribuzin.

* * * * *

UNITED STATES PATENT AND TRADEMARK OFFICE
CERTIFICATE OF CORRECTION

PATENT NO. : 4,614,799
DATED : September 30, 1986
INVENTOR(S) : Stanley Tocker

It is certified that error appears in the above—identified patent and that said Letters Patent is hereby corrected as shown below:

Claim 1, at column 8, lines 30 to 57 should be replaced with the following claim which is the only independent claim that was allowed.

--Claim 1. A process for the preparation of a surface-modified particulate form of a compound of the Formula I

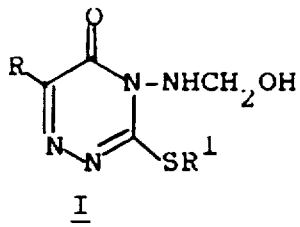

where R is $C_3-C_6$ alkyl and $R^1$ is $C_1-C_2$ alkyl, comprising:

(a) mixing a compound of Formula I, in particulate form, in water; and (b) treating the mixture, at a temperature of about 15-90°C, with a base to provide a pH of about 11-13 or with a mineral acid to provide a pH of about 0.5-2.0.--

Signed and Sealed this

Twenty-seventh Day of January, 1987

Attest:

DONALD J. QUIGG

Attesting Officer         Commissioner of Patents and Trademarks